United States Patent [19]

Vincent et al.

[11] Patent Number: 4,914,214

[45] Date of Patent: Apr. 3, 1990

[54] PROCESS FOR THE INDUSTRIAL SYNTHESIS OF PERINDOPRIL

[75] Inventors: Michel Vincent, Bagneux; Jean Baliarda, Anthony; Bernard Marchand, Checy; Georges Remond, Versailles, all of France

[73] Assignee: Adir Et Cie, Neuilly-sur-Seine, France

[21] Appl. No.: 245,446

[22] Filed: Sep. 16, 1988

[30] Foreign Application Priority Data

Sep. 17, 1987 [FR] France ................................ 87 12896

[51] Int. Cl.$^4$ .......................................... C07D 209/18
[52] U.S. Cl. .................................................. 548/492
[58] Field of Search ......................................... 548/492

*Primary Examiner*—David B. Springer
*Attorney, Agent, or Firm*—Gordon W. Hueschen

[57] ABSTRACT

Process for the industrial synthesis of perindopril, in which (2S,3aS,7aS)-2-carboxyperhydroindole is condensed with N-[(S)-1-carbethoxybutyl]-(S)-alanine after protection of the carboxyl group, the product resulting from the condensation being then subjected to deprotection of the carboxyl carried by the heterocyclic ring. The (2S,3aS,7aS)-2-carboxyperhydroindole and N-[(S)-1-carbethoxybutyl]-(S)-alanine are themselves obtained in excellent conditions from 2-carboxyindole and from L-alanine respectively, both available on an industrial scale.

5 Claims, No Drawings

PROCESS FOR THE INDUSTRIAL SYNTHESIS OF PERINDOPRIL

The present invention relates to a process for the industrial synthesis of perindopril of formula (I):

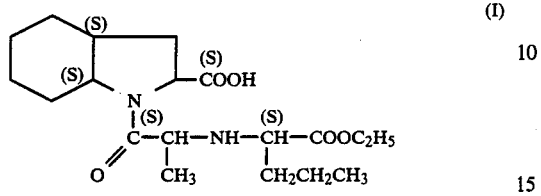

or (2S,3aS,7aS)-1-{2-[1-(ethoxycarbonyl)-(S)-butylamine]-(S)-propionyl}octahydroindole-2-carboxylic acid and its tert-butylamine salt.

The compound of formula (I) and its addition salts and, more particularly, its tert-butylamine salt have interesting pharmacological properties. They exert an inhibiting activity on certain enzymes, such as carboxypeptidases, enkephalinases or kininase II. In particular, they inhibit the conversion of the angiotensin I decapeptide to angiotensin II octapeptide, which is responsible in certain cases for arterial hypertension, by acting on the conversion enzyme.

The use of these compounds in therapeutics makes it possible, therefore, to reduce or even to suppress the activity of these enzymes, which are responsible for the hypertensive disorder or for cardiac insufficiency.

In particular, the compound of formula (I) is distinguished from other conversion enzyme inhibitors by the intensity and the duration of its action.

The compound of formula (I), its preparation and its use in therapeutics have been described in European Patent No. 0,049,658.

However, the industrial preparation of a derivative such as the compound of formula (I) requires an indepth study of all the reaction stages, of the choice of the starting materials, of the reactants, and of the solvents which make it possible to obtain optimum yields.

The Applicant Company has found a process for the synthesis of the compound of formula (I), in which these conditions have been combined through the use of a set of particularly advantageous methods and processes.

In particular, one of the starting materials which can be employed for the preparation of the compounds of formula (I) is 2-carboxyperhydroindole, described in European Patent Application 0,037,231, or one of its esters of formula (II):

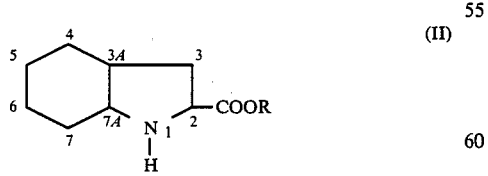

where R denotes a hydrogen atom or a lower alkyl or benzyl group.

The compound of formula (II) exists in the form of four racemic pairs:
 the two cis IIa and IIb epimers,
 the two trans IIc and IId epimers,

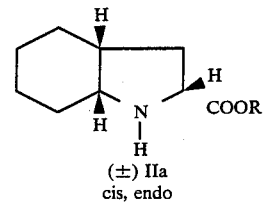

(±) IIa
cis, endo
2S, 3aS, 7aS or 2R, 3aR, 7aR

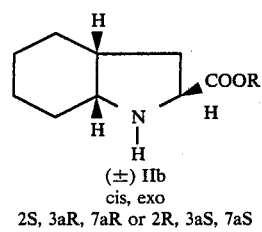

(±) IIb
cis, exo
2S, 3aR, 7aR or 2R, 3aS, 7aS

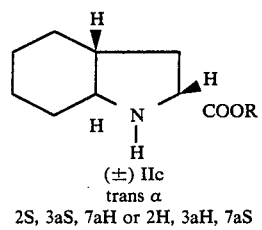

(±) IIc
trans α
2S, 3aS, 7aH or 2H, 3aH, 7aS

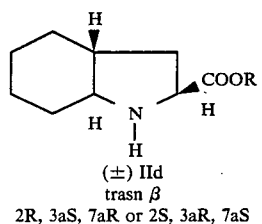

(±) IId
trasn β
2R, 3aS, 7aR or 2S, 3aR, 7aS

The preparation of a compound of formula (II) can be carried out by means of well-known methods of the prior art (EP 0,037,231, EP 0,084,164, EP 0,115,345, EP 0,173,199, EP 0,132,580).

However, the isomer which is specifically employed in the synthesis of the compound of formula (I), on account of its structure, is (2S,3aS,7aS)-2-carboxyperhydroindole of formula (IIaS):

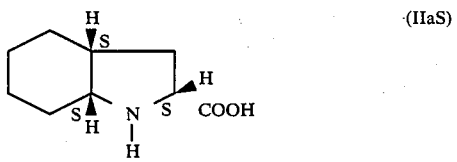

The preparation of (2S,3aS,7aS)-2-carboxyperhydroindole can be carried out according to the methods described in the prior art (EP 0,037,231, EP 0,115,345, EP 0,173,199, EP 0,132,580).

The starting material employed by some of these is 2-carboxyindole which has the advantage of being a starting material which is readily available and relatively inexpensive (EP 0,037,231), which is subjected to catalytic reduction over rhodium to give a mixture of the two cis endo isomers of (2S,3aS,7aS) and (2R,3aR,7aR) configuration respectively.

However, the separation of the (2S,3aS,7aS) isomer which can be used in the synthesis of the compound of formula (I) from the (2R,3aR,7aR) isomer generally requires the use of methods which are particularly arduous to employ.

Thus, to perform this separation of the (2S,3aS,7aS) and (2R,3aR,7aR) (cis, endo racemic) isomers, Patent No. 0,037,231 employs many stages requiring the synthesis of the N-benzoyl compound, fractional crystallization of the salt formed by the diastereoisomer with S-α-phenylethylamine, the liberation of the two N-benzoylated SSS and RRR compounds, and then the removal of the benzoyl group, followed by a pass through an ion exchange column and a recrystallization.

For this same separation, European Patent Application No. 0,115,345 employs several stages requiring the esterification of the carboxylic acid group with benzyl alcohol, the conversion of the amino ester to a salt with (S)-N-benzyloxycarbonylphenylalanine, the separation of the S,S,S isomer by fractional crystallization, and the liberation of the amino group, optionally followed by the liberation of the carboxylic acid group.

To synthesize the compound of formula (I) on an industrial scale, the Applicant Company employs an original process for the synthesis of (2S,3aS,7aS)-2-carboxyperhydroindole, which also offers the advantage of employing 2-carboxyindole as starting material, but which does not offer the disadvantage of this arduous separation of the two (2S,3aS,7aS) and (2R,3aR,7aR) isomers, because, in a first step, 2-carboxyindole is reduced to 2-carboxyindoline, to give a mixture of 2R and 2S carboxyindolines which are easily separated in a single stage, by fractional crystallization. The 2S isomer is then subjected to catalytic hydrogenation to lead stereoselectively to (2S,3aS,7aS)-2-carboxyperhydroindole.

More particularly, the starting material employed in the industrial synthesis of (2S,3aS,7aS)-2-carboxyperhydroindole, employed by the Applicant Company for the industrial synthesis of the compound of formula (I), is 2-carboxyindole or one of its esters of formula (III):

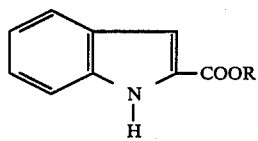
(III)

in which R denotes a hydrogen atom or a lower alkyl group, which is subjected to reduction by a process such as the use of the tin/hydrochloric acid couple, preferably in a lower aliphatic alcohol medium, preferably at ambient temperature, to (R,S)-2-carboxyindoline or to one of its esters of formula (IV):

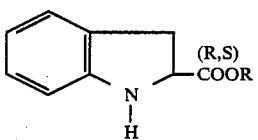
(IV)

in which R has the same meaning as in formula (III), which, when R=H, is the 2-carboxyindoline of formula (V), which, when R is other than H, is converted by alkaline hydrolysis into 2-carboxyindoline of formula (V):

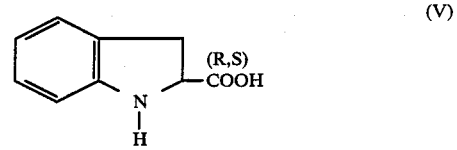
(V)

consisting, in fact, of a mixture of two isomers, according to whether the carboxyl-bearing carbon is:
in the R configuration (R isomer),
in the S configuration (S isomer),
from which mixture the S isomer is isolated by adding the said mixture to a solution of (+)-α-methylbenzylamine in a lower aliphatic alcohol, to obtain a precipitate of the salt formed by (S)-2-carboxyindoline with α-methylbenzylamine,
which, after filtration, is dissolved in water, the solution obtained being then acidified to permit the liberation of (S)-2-carboxyindoline,
which, after filtration and washing, is subjected to catalytic hydrogenation,
under a hydrogen pressure of between 10 and 150 bars, preferably chosen between 20 and 60 bars,
with heating to a temperature of between 30° and 100° C., preferably between 40° and 80° C.,
the catalyst being chosen from rhodium, palladium, platinum or nickel, mixed with a support such as charcoal, so as to make it possible to obtain a maximum proportion of (2S,3aS,7aS)-2-carboxyperhydroindole, the latter being separated from the (2S,3aR,7aR) isomer obtained in a low proportion by a single crystallization from a polar solvent strictly chosen from lower aliphatic alcohol, acetonitrile, ethyl acetate and dioxane, by itself or mixed with water, or mixed with each other and with water, provided that the mixture obtained forms a single phase.

The second starting material employed for the synthesis of the compound of formula (I) according to the invention is the compound of formula (VI):

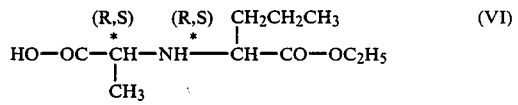
(VI)

The compound of formula (VI) exists in the form of four stereoisomers which may be denoted as (R,R) (R,S), (S,R) or (S,S) according to the configuration of the two so-called asymmetric carbons.

Now, the most active compound of formula (I) is that in the case of which the two carbons in the side chain both have the S configuration.

This is the reason why the process for the industrial synthesis of the compound of formula (I) according to the invention concerns exclusively the industrial synthesis of the compound of formula (VI), in which the two asymmetric carbons both have the S configuration.

No process for the specific industrial synthesis of the compound of formula (VI) has been described. European Patent Application No. 0,117,488, which is very general and which employs α-carboxylated trifluoromethanesulfonates, is known. However, the stereochemistry of both starting materials must be strictly chosen in order to obtain the desired diastereoisomer of the product of formula (I).

It is furthermore known to a person skilled in the art that, as a very general rule, to permit the separation of diastereoisomers which are obtained in the course of syntheses where the stereochemistry of the starting materials is not fixed beforehand, traditional techniques such as fractional crystallization or chromatography on a silica column are resorted to.

In the case of the industrial synthesis of the compound of the formula (I), the Applicant Company employs a process for the industrial synthesis of the compound of formula (VI) which is of great interest because, on the one hand, it is particularly simple to implement and, on the other hand, it makes possible, by means of a judicious choice of the reactants (catalysts and solvents) employed to obtain the (S,S) diastereoisomer directly in yields which are highly advantageous on an industrial scale.

Furthermore, the synthesis according to the process of the invention offers the advantage of employing inexpensive compounds as starting materials, and this is of importance on an industrial scale.

More particularly, the starting material employed in the process employed by the Applicant Company for the industrial synthesis of the compound of formula (I) is a compound of a natural amino acid, of formula (VII):

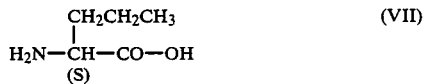

in which the asymmetric carbon has the S configuration, since it is well known to a person skilled in the art that the carboxyl-bearing carbon in natural amino acids has the S configuration (with the exception of cysteine), which is treated, in the presence of an acidic esterification catalyst, and preferably of thionyl chloride, with ethanol, which is industrially available at a low price, to give the ester of formula (VIII):

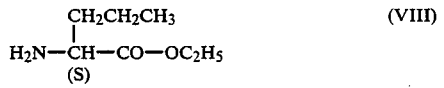

which is condensed under catalytic hydrogenation, under a hydrogen pressure of between 10 and 150 bars, preferably chosen between 20 and 60 bars, preferably at ambient temperature,
the catalyst being chosen from rhodium, palladium, platinum or nickel, mixed with a support such as charcoal, a catalyst carefully chosen so as to direct the selectivity of the reaction, thus making it possible to obtain a maximum proportion of the (S,S) diastereoisomer,
with pyruvic acid $CH_3-CO-COOH$, a natural, inexpensive and industrially available product, to lead directly, after a single crystallization from a solvent carefully chosen from lower aliphatic alcohol, acetonitrile, ethyl acetate and dioxane, by itself or mixed with water, or mixed with each other and with water, provided that the mixture obtained forms a single phase, cooling and filtration, solely to the (S,S) diastereoisomer of the compound of formula (VI).

The final stage of the industrial synthesis of the compound of formula (I) according to the invention consists in the condensation of the compound of formula (IIaS), whose carboxylic acid group has been protected beforehand by esterification with an alcohol EOH, where E preferably denotes a linear or branched lower alkyl or benzyl group in the presence of an acidic esterification catalyst, to give an ester of (2S,3aS,7aS)-2-carboxyperhydroindole of formula (IX):

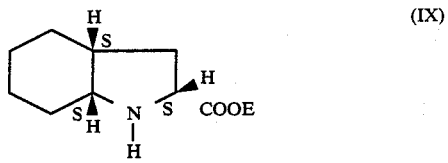

which is condensed directly with the compound of formula (VI) in an alkaline medium in the presence of a catalyst for peptide synthesis such as dicyclohexylcarbodiimide, to lead to the derivative of formula (X):

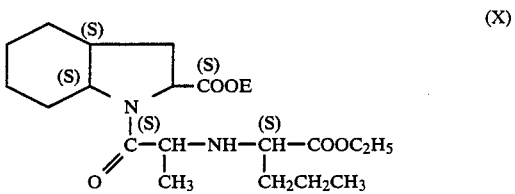

in which E has the same meaning as in formula (IX), which is subjected to deprotection of the carboxylic group of the heterocyclic ring, to lead the compound of formula (I), in the form of a base,
which is dissolved in a solvent chosen from lower aliphatic alcohol, acetonitrile, ethyl acetate, dioxane by itself or mixed with each other, before the addition of tert-butylamine,
the salt thus obtained being crystallized by heating the reaction mixture, filtering hot, cooling and finally filtering off.

The following example illustrates the invention, but does not limit it in any way.

EXAMPLE

Industrial Synthesis of the tert-Butylamine Salt of (2S,3aS,7aS)-1-2-[1-(ethoxycarbonyl)-(S)-butylamino]-(S)-propionyl}-octahydroindole-2-carboxylic acid Stage 1: (2S,3aS,7aS)-2-Carboxyoctahydroindole Stage 1a: 2-Ethoxycarbonylindole Heat 5 kg of 2-carboxyindole suspended in ethanol in the presence of sulfuric acid to boiling for 8 hours. Evaporate.

Evaporate off the ethyl acetate, take up the crystalline mass with hexane. After filtering off and drying, 5.3 kg of crystals are obtained.

Melting point: 123°–125° C.

Microanalysis: Calculated: C % 69.83; H % 5.86; N % 7.40; Found: C % 69.56; H % 5.74; N % 7.30.

Spectrometry in the infrared: 2150 $cm^{-1}$ (NH); 1680 $cm^{-1}$ (carboxylic acid).

Stage 1B: (R,S)-2-Ethoxycarbonylindoline

Suspend, in a reactor, 10 kg of 2-ethoxycarbonylindoline obtained previously in 110 liters of hydrochloric ethanol. Next, add 20 kg of granulated tin. Keep stirring for approximately 2 days at ambient temperature.

Evaporate off the ethanol, take up the residue with water and add 110 liters of toluene. Stir for approximately 20 minutes. Alkalify with aqueous ammonia.

Separate off the aqueous phase and extract once again with 150 liters of toluene.

Combine the toluene phases and wash them with water. Separate off the toluene phases, filter. Remove the water by distilling the water-toluene azeotrope. Cool and pass through a stream of anhydrous HCl gas.

Cool. Evaporate down and wash with pure toluene.

Weight obtained: 10.11 kg.

Yield: 84%.

Thin layer chromatography: Solvent: toluene: 10; ethyl acetate: 5; Support: Merck silica 60 F 254; Developer: UV; $R_f$: 0.55.

Stage 1C: (R,S)-2-Carboxyindoline 2.15 kg of (R,S)-2-ethoxycarbonylindoline dissolved in ethanol are saponified with 12.5 liters of N sodium hydroxide with stirring for 24 hours. After washing the alkaline solution, neutralize with concentrated hydrochloric acid. After filtering off, washing and drying, 1.57 kg of white crystals of the expected product are obtained.

Yield: 86%.

Melting point: 188°–189° C.

Spectrometry in the infrared: $NH_2+$: 2500–2000 $cm^{-1}$; $COO-$: 1620 $cm^{-1}$.

Stage 1D: (S)-2-Carboxyindoline 6.05 kg of (R,S)-2-carboxyindoline are added to a solution of 4.49 kg of (+)-α-methylbenzylamine in anhydrous ethanol. A white precipitated product is obtained which, after filtering off, is digested in refluxing isopropanol. After cooling, the solid is filtered off and washed with a little isopropanol; the white crystals obtained are dried: 3.68 kg.

Rotatory power: $[\alpha]_{21}^D = -5.3$ (c=1% ethanol).

(S)-2-Carboxyindoline is prepared in a quantitative yield by dissolving 1 kg of the above salt in 5 liters of water and neutralizing with an aqueous hydrochloric acid solution. This precipitate is filtered off, washed with water and dried.

Stage 1E: (2S,3aS,7aS)-2-Carboxyoctahydroindole

Place 25 kg of (S)-2-carboxyindoline, obtained previously, in 110 liters of methanol in a vessel. Keep stirred. Charge the rhodium (5% dry) catalyst into a mixer.

Start up the stirring in a hydrogenator, charge the methanolic suspension of (S)-2-carboxyindoline by passing it through the mixer and rinse the assembly with water. Heat to 60° C. and pressurize with hydrogen (30 bars).

Filter off the catalyst on a single-plate filter. Collect the hydroalcoholic liquors in a reactor and evaporate the methanol off under vacuum.

After concentrating, charge approximately 300 kg of dioxane. Heat to boiling and add water until a solution is obtained. Allow to cool. Filter off and dry. 22.3 kg of crystals are obtained.

Yield: 86.1%.

Stage 2: N-[(S)-1-Carbethoxybutyl]-(S)-alanine

Stage 2A: Ethyl L-norvalinate hydrochloride

Place 35 kg of L-norvaline in approximately 300 kg of denatured ethanol in a reactor. Introduce approximately 60 kg of thionyl chloride, slowly and gradually.

After stirring for a quarter of an hour, heat to reflux for 3 hours and then evaporate off the ethanol under vacuum.

Take up the residue with 300 liters of cyclohexane and heat to boiling. Allow to cool, filter, wash with cyclohexane and dry. 52.9 kg of ethyl L-norvalinate hydrochloride are obtained, that is a 97.6% yield.

The product thus obtained is employed as such in the next stage.

Stage 2B: N-[(S)-1-carbethoxybutyl]-(S)-alanine

Place 45 kg of ethyl N-norvalinate hydrochloride obtained in the preceding stage and approximately 110 liters of water in a vessel equipped with a stirrer.

Alkalify, then pour 23 kg of pyruvic acid very gradually into the solution obtained previously and stir the reaction mixture for 30 minutes.

Place an aqueous suspension of charcoal containing 5% palladium and the alkaline solution of ethyl L-norvalinate obtained previously in a hydrogenation apparatus.

Hydrogenate under pressure (30 bars) at ambient temperature for approximately one day.

Filter under vacuum and evaporate the filtrate under reduced pressure, filter off and dry. Treat the residue obtained with ethanol; remove the insoluble material, consisting of sodium chloride, by filtration and rinse it with ethanol. Combine the ethanolic solutions; evaporate off the ethanol under reduced pressure and crystallize the residue from acetonitrile.

34.3 kg of N-[(S)-1-carbethoxybutyl]-(S)-alanine are obtained, that is 63.9% yield.

Stage 3: tert-Butylamine salt of (2S,3aS,7aS)-1-{2-[1-ethoxycarbonyl)-(S)-butylamino]-(S)-propionyl}octahydroindole-2-carboxylic acid

Stage 3A: para-Toluenesulfonate of the benzyl ester of (2S,3aS,7aS)-2-carboxyoctahydroindole In a 30-liter reactor, reflux 12.5 kg of (2S,3aS,7aS)-2-carboxyperhydroindole, 50 kg of para-toluenesulfonic acid and 14.2 kg of benzyl alcohol and 38.4 kg of toluene, removing the water formed with the aid of a continuous separator. When no more water separates out, cool, filter off the precipitate formed, and dry.

Yield: 91.3%.

Stage 3B: Benzyl ester of (2S,3aS,7aS)-1-{2-[1-(ethoxycarbonyl)-(S)-butylamino]-(S)-propionyl}octahydroindole-2-carboxylic acid Add approximately 3.5 kg of triethylamine to a suspension of approximately 5 kg of para-toluenesulfonate of the benzyl ester of (2S,3aS,7aS)-2-carboxyoctahydroindole in approximately 60 kg of ethyl acetate, followed by approximately 6 kg of 1-hydroxybenzotriazole, approximately 7.5 kg of the N-[(S)-1-carbethoxybutyl]-(S)-alanine obtained in stage 2 and approximately 7.0 kg of dicyclohexylcarbodiimide.

Stir, cooling slightly for approximately 3 hours, then filter off the dicyclohexylurea formed by filtration and wash the organic phase with water. The dried organic phase is evaporated to dryness.

Yield: 92.3%.

Stage 3C: (2S,3aS,7aS)-1-{2-[1-(Ethoxycarbonyl)-(S)-butylamino]-(S)-propionyl}octahydroindole-2-carboxylic acid Dissolve, in a hydrogenator, 14 kg of benzyl ester of the (2S,3aS,7aS)-1-{2-[1-(ethoxycarbonyl)-(S)- butylamino]-(S)-propionyl}octahydroindole-2-carboxylic acid obtained in the preceding stage in cyclohexane.

Add the charcoal containing 5% palladium and approximately 50 liters of water. Hydrogenate at ordinary temperature and pressure until the theoretical volume of hydrogen has been absorbed. Filter, wash the insoluble material with cyclohexane, separate off the organic phase and wash the aqueous phase again with cyclohexane. Isolate the product from the aqueous phase by freeze-drying.

Stage 3D: tert-Butylamine salt of (2S,3aS,7aS)-1-{2-[1-(ethoxycarbonyl)-(S)-butylamino]-(S)-propionyl}octahydroindole-2-carboxylic acid Place in a reactor approximately 140 liters of ethyl acetate and 10 kg of (2S,3aS,7aS)-1-{2-[1-ethoxycarbonyl)-(S)-butylamino]-(S)-propionyl}octahydroindole-2-carboxylic acid obtained previously. Add gradually approximately 2.20 kg of tert-butylamine, heat to reflux until all has dissolved; filter. Cool, filter off and dry.

Yield: 95%.

I claim:

1. Process for the synthesis of the tert-butylamine salt of (2S,3aS,7aS)-1-{2-[1-(ethoxycarbonyl)-(S)-butylamino]-(S)-propionyl}octahydroindole-2-carboxylic acid of formula (I):

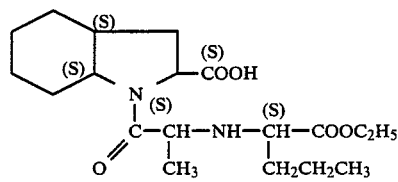

wherein (2S,3aS,7aS)-2-carboxyperhydroindole of formula (IIaS)

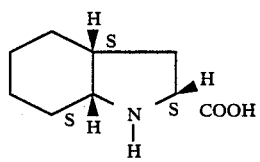

is protected by esterification with an alcohol EOH, where E denotes a linear or branched lower alkyl group or the benzyl group, in the presence of an acidic esterification catalyst to give an ester of (2S,3aS,7aS)-2-carboxyperhydroindole of formula (IX):

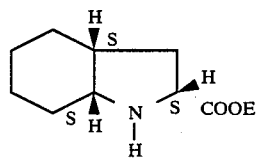

is condensed with to the (S,S) diastereoisomer of N-[(S)-1-carbethoxybutyl]-(S)-alanine of formula (VI):

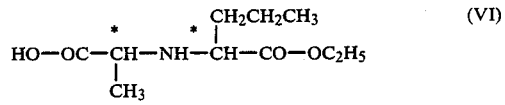

in an alkaline medium in the presence of a catalyst for peptide synthesis such as dicyclohexylcarbodiimide in the presence of 1-hydroxybenzotriazole to lead to the compound of formula (X):

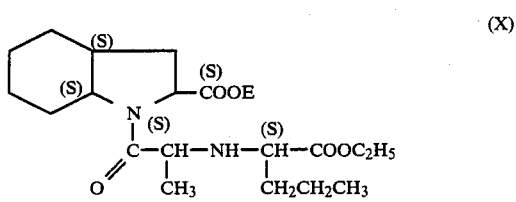

in which E has the same meaning as in formula (IX), which is subjected to deprotection of the carboxylic group of the heterocyclic ring, to lead to the compound of formula (I) in the form of a base, which is dissolved in a solvent chosen from lower aliphatic alcohol, acetonitrile, ethyl acetate, dioxane by itself or mixed with each other, before the addition of tert-butylamine, the salt thus obtained being crystallized by heating the reaction mixture, filtering hot, cooling and finally filtering off.

2. A process for the synthesis of the tert-butylamine salt of (2S,3aS,7as)-1-{2-[1-(ethoxycarbonyl)-(S)-butylamino]-(S)-propionyl}octahydroindole-2-carboxylic acid, as claimed in claim 1, wherein the carboxylic acid group of (2S,3aS,7aS)-2-carboxyperhydroindole preceding the condensation of the latter with N-[(S)-1-carbethoxybutyl]-(S)-alanine of formula (VIII), is protected by reaction with benzyl alcohol.

3. A process for the synthesis of the tert-butylamine salt of (2S,3aS,7aS)-1-{2-[1-(ethoxycarbonyl)-(S)-butylamino]-(S)-propionyl}octahydroindole-2-carboxylic acid, as claimed in one of claim 1 or 2, wherein the carboxylic acid group of (2S,3aS,7aS)-2-carboxyperhydroindole preceding the condensation of the latter with N-[(S)-1-carbethoxybutyl]-(S)-alanine of formula (VIII) is protected by reaction with benzyl alcohol, using paratoluenesulfonic acid as catalyst.

4. A process for the synthesis of the tert-butylamine salt of (2S,3aS,7aS)-1-{2-[1-(ethoxycarbonyl)-(S)-butylamino]-(S)-propionyl}octahydroindole-2-carboxylic acid, as claimed in one of claim 1, 2, or 3, wherein the deprotection of the carboxylic acid group of (2S,3aS,7aS)-2-carboxyperhydroindole following the condensation of the latter with N-[(S)-1-carbethoxybutyl]-(S)-alanine of formula (VIII) is performed by catalytic hydrogenation.

5. A process for the synthesis of the tert-butylamine salt of (2S,3aS,7aS)-1-{2-[1-(ethoxycarbonyl)-(S)-butylamino]-(S)-propionyl}octahydroindole-2-carboxylic acid, as claimed in one of claim 1, 2, 3, or 4, wherein the deprotection of the carboxylic acid group of (2S,3aS,7aS)-2-carboxyperhydroindole following the condensation of the latter with N-[(S)-1-carbethoxybutyl]-(S)-alanine of formula (VIII) is performed by catalytic hydrogenation at ambient temperature and pressure, in the presence of palladized charcoal.

* * * * *

UNITED STATES PATENT AND TRADEMARK OFFICE
CERTIFICATE OF CORRECTION

PATENT NO. : 4,914,214

DATED : April 3, 1990

INVENTOR(S) : Michel Vincent, Jean Baliarda, Bernard Marchand, Georges Remond

It is certified that error appears in the above-identified patent and that said Letters Patent is hereby corrected as shown below:

Column 2, line 28; "7aH or 2H, 3aH" should read
-- 7aR or 2R, 3aR --.

Column 5, line 13; "makes possible" should read
-- makes it possible --

Column 5, line 15; "employed to obtain" should read
-- employed, to obtain --.

Column 9, line 67; delete "to"

Col. 1, line 37; "therapeutics have" should read -- therapeutics, have --

Signed and Sealed this

Second Day of July, 1991

*Attest:*

HARRY F. MANBECK, JR.

*Attesting Officer*  *Commissioner of Patents and Trademarks*